US011291847B2

(12) United States Patent
Caparso et al.

(10) Patent No.: US 11,291,847 B2
(45) Date of Patent: Apr. 5, 2022

(54) SYSTEMS AND METHODS FOR PREVENTING, DIAGNOSING, AND/OR TREATING ONE OR MORE MEDICAL CONDITIONS VIA NEUROMODULATION

(71) Applicant: The Regents of the University of Colorado, Denver, CO (US)

(72) Inventors: Anthony V. Caparso, Avon, OH (US); Malik Kahook, Denver, CO (US); Naresh Mandava, Aurora, CO (US); Noah Lemire, Columbus, OH (US); Adam Farwick, Cincinnati, OH (US); Steve Wilder, Blacklick, OH (US); Steve Risser, Reynoldsburg, OH (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 175 days.

(21) Appl. No.: 15/851,842

(22) Filed: Dec. 22, 2017

(65) Prior Publication Data

US 2018/0133478 A1    May 17, 2018
US 2020/0188670 A9    Jun. 18, 2020

Related U.S. Application Data

(63) Continuation-in-part of application No. 15/180,451, filed on Jun. 13, 2016, now Pat. No. 10,004,634.
(Continued)

(51) Int. Cl.
*A61N 1/36* (2006.01)
*A61N 1/372* (2006.01)
(Continued)

(52) U.S. Cl.
CPC ......... *A61N 1/3787* (2013.01); *A61N 1/0526* (2013.01); *A61N 1/0551* (2013.01);
(Continued)

(58) Field of Classification Search
CPC .............. A61N 1/3787; A61N 1/37211; A61N 1/37229; A61N 1/0551; A61N 1/36046;
(Continued)

(56) References Cited

U.S. PATENT DOCUMENTS 4,819,661 A    4/1989  Heil, Jr. et al.
5,193,539 A    3/1993  Schulman et al.
(Continued)

FOREIGN PATENT DOCUMENTS

CN    103747834 A    4/2014
JP    2014-514070 A   6/2014
(Continued)

OTHER PUBLICATIONS

Gupta, et al. "Nasolacrimal Stimulation of Aqueous Tear Production" Cornea 16(6) pp. 645-648, 1997.
(Continued)

*Primary Examiner* — Jennifer Pitrak McDonald
*Assistant Examiner* — Pamela M. Bays

(57) ABSTRACT

Described are systems and methods for preventing, diagnosing, and/or treating one or more medical conditions. The medical conditions can be ocular and/or neurological diseases, disorders, and/or conditions. The systems and methods can employ a microstimulator that is configured to be placed within an anatomical structure of a subject. The microstimulator can be capacitively linked to an external electronic device to provide neuromodulation to a biological target site proximal to the anatomical structure. The microstimulator can include a body and an electrically conductive insert arranged within the body to create a capacitively (Continued)

coupled link with the external electronic device. The electrically conductive insert can receive a power signal from an external electronic device and convert the power signal to deliver a therapy signal to the biological target site.

16 Claims, 9 Drawing Sheets

Related U.S. Application Data

(60) Provisional application No. 62/589,877, filed on Nov. 22, 2017, provisional application No. 62/321,961, filed on Apr. 13, 2016, provisional application No. 62/180,265, filed on Jun. 16, 2015.

(51) Int. Cl.
| | | |
|---|---|---|
| *A61N 1/378* | (2006.01) | |
| *A61N 1/32* | (2006.01) | |
| *A61N 1/375* | (2006.01) | |
| *A61N 1/05* | (2006.01) | |
| *A61B 3/10* | (2006.01) | |
| *A61B 3/16* | (2006.01) | |
| *A61F 9/00* | (2006.01) | |
| *A61F 9/007* | (2006.01) | |

(52) U.S. Cl.
CPC ..... *A61N 1/36046* (2013.01); *A61N 1/37205* (2013.01); *A61N 1/37211* (2013.01); *A61N 1/37229* (2013.01); *A61B 3/101* (2013.01); *A61B 3/16* (2013.01); *A61F 9/0017* (2013.01); *A61F 9/0026* (2013.01); *A61F 9/00772* (2013.01); *A61N 1/328* (2013.01); *A61N 1/36057* (2013.01); *A61N 1/36071* (2013.01); *A61N 1/36075* (2013.01); *A61N 1/3756* (2013.01)

(58) Field of Classification Search
CPC . A61N 1/37205; A61N 1/0526; A61F 9/0017; A61F 9/0772; A61F 9/0026
See application file for complete search history.

(56) References Cited

U.S. PATENT DOCUMENTS

| | | |
|---|---|---|
| 5,193,540 A | 3/1993 | Schulman et al. |
| 2006/0085041 A1* | 4/2006 | Hastings ............ A61N 1/37223 607/33 |
| 2006/0184211 A1* | 8/2006 | Gaunt ...................... A61N 1/05 607/48 |
| 2007/0173904 A1* | 7/2007 | Pilla ......................... A61N 2/02 607/50 |
| 2008/0103376 A1 | 5/2008 | Felder |
| 2009/0099626 A1 | 4/2009 | De Juan, Jr. et al. |
| 2009/0216296 A1 | 8/2009 | Meskens |
| 2010/0198298 A1 | 8/2010 | Glukhovsky et al. |
| 2010/0310622 A1 | 12/2010 | Chauhan et al. |
| 2011/0060392 A1 | 3/2011 | Zdeblick et al. |
| 2011/0130804 A1 | 6/2011 | Lin et al. |
| 2013/0006326 A1* | 1/2013 | Ackermann ....... A61N 1/36046 607/53 |
| 2013/0123882 A1 | 5/2013 | Towe |
| 2013/0296977 A1 | 11/2013 | Chiu et al. |
| 2014/0200626 A1 | 7/2014 | Campbell et al. |
| 2016/0344240 A1 | 11/2016 | Yeh et al. |

FOREIGN PATENT DOCUMENTS

| | | | |
|---|---|---|---|
| WO | 00/13585 A1 | 3/2000 | |
| WO | 2004/002572 A1 | 1/2004 | |
| WO | WO-2015179225 A1 * | 11/2015 | ........... A61N 1/3787 |

OTHER PUBLICATIONS

John Whitwell "Role of the Sympathetic in Lacrimal Secretion" Brit. J. Ophthal 1961. vol. 45, p. 439.
M.S. Arenson et al. "The Parasympathetic Secretory Nerves of the Lacrimal Gland of the Cat" J. Physiol 1970. vol. 217, pp. 201-212.
PCT International Search Report and Written Opinion for corresponding International Application No. PCT/US2017/068151, dated Feb. 22, 2018, pp. 1-13.
Chinese Patent Application No. 201680040343.8, Office Action, 9 pages, dated Sep. 3, 2020.
Japanese Patent Application No. 2017-565074, Office Action, 3 pages, dated Sep. 1, 2020.

* cited by examiner

SYSTEMS AND METHODS FOR PREVENTING, DIAGNOSING, AND/OR TREATING ONE OR MORE MEDICAL CONDITIONS VIA NEUROMODULATION

RELATED APPLICATIONS

This application claims the benefit of U.S. Provisional Application No. 62/589,877, filed Nov. 22, 2017, entitled "Nasolacrimal Tear Microstimulator", the entirety of which is hereby incorporated by reference for all purposes.

This application is also a Continuation in Part of U.S. patent application Ser. No. 15/180,451, filed Jun. 13, 2016, and now issued as U.S. Patent No. 10,004,634, and entitled "Nasolacrimal Implants and Related Methods for Tear Stimulation", which claims priority to U.S. Provisional Applications 62/321,961, filed Apr. 13, 2016, and 62/180,265, filed Jun. 16, 2015. These applications are each incorporated by reference herein in their entirety.

TECHNICAL FIELD

The present disclosure relates generally to systems and methods for preventing, diagnosing, and/or treating one or more medical conditions via neuromodulation. The systems and methods of the present disclosure can be used, as an example, to use neuromodulation to induce tear production to treat or prevent the medical condition of dry eye disease.

BACKGROUND

Dry eye disease is a condition resulting from a disruption of the natural tear film on the ocular surface, leading to ocular discomfort, visual disturbance, and/or a reduction in vision-related quality of life. The disruption in the natural tear film may prevent healthy gas exchange and nutrient transport, promote cellular desiccation, and/or create a poor refractive surface for vision. Such disruption in the natural tear film can be due to an imbalance between tear production from the lacrimal glands and evaporation or drainage by the Meibomian glands, which may be caused by or secondary to post-menopausal hormonal deficiency, auto-immune disease, LASIK surgery, or the like. The disruption of the natural tear film may cause a low tear volume, which causes a hyperosmolar environment that may induce an inflamed state of the ocular surface. Such an inflammatory response may induce apoptosis of ocular surface cells, which, in turn, prevent proper distribution of the tear film on the ocular surface, such that any available tear volume delivered to the ocular surface may be rendered less effective initiating a vicious cycle in which more inflammation can ensue, causing more ocular surface damage. Additionally, the neural control loop, which controls reflex tear activation, may be disrupted because the sensory neurons in the ocular surface are damaged, resulting in fewer tears being secreted, and another vicious cycle may develop, resulting in further progression of dry eye disease, in which fewer tears may cause nerve cell loss, which may result in even fewer tears.

A wide spectrum of treatments options exist for dry eye disease, including: artificial tear substitutes, ointments, gels, warm compresses, environmental modification, topical cyclosporine, omega-3 fatty acid supplements, punctal plugs, moisture chamber goggles, punctal cautery, systemic cholinergic antagonists, systemic anti-inflammatory agents, mucolytic agents, autologous serum tears, scleral contact lenses, and tarsorrhaphy. Although the current treatment options are numerous, such treatment options have limited effectiveness and generally provide only mild symptom relief or improvement in ocular health over a short period of time.

SUMMARY

The present disclosure relates generally to systems and methods for preventing, diagnosing, and/or treating one or more medical conditions.

In one aspect, the present disclosure can include a microstimulator that is configured to be placed within an anatomical structure of a subject. The microstimulator can be capacitively linked to an external electronic device to provide neuromodulation to a biological target site proximal to the anatomical structure. The microstimulator can include a body and an electrically conductive insert arranged within the body to create a capacitively coupled link to the external electronic device. The electrically conductive insert can receive a power signal from an external electronic device and convert the power signal to deliver a therapy signal to the biological target site.

In another aspect, the present disclosure can include a system for capacitive power transfer. The system can include an external electronic device capacitively coupled to a microstimulator that is configured to be placed within an anatomical structure of a subject. The microstimulator can include a body and an electrically conductive insert arranged within the body to create a capacitively coupled link with the external electronic device. The electrically conductive insert can receive a power signal from an external electronic device and convert the power signal to deliver a therapy signal to the biological target site. The microstimulator can be configured to be placed within an anatomical structure of a subject and can include a body and an electrically conductive insert. The electrically conductive insert can be arranged within the body to create a capacitively coupled link with the external electronic device. The electrically conductive insert can receive a power signal from the external electronic device and converts the power signal to deliver a therapy signal to a biological target site proximal to the anatomical structure.

In a further aspect, the present disclosure can include a method for powering an implantable microstimulator. The method can include the steps of establishing a connection between an external electronic device and the implantable microstimulator through a conductive biological material; and capacitively linking the external electronic device with the implantable microstimulator to deliver a power signal from the external electronic device to the implantable microstimulator.

In yet another aspect, the present disclosure can include a method for treating, diagnosing, or preventing a medical condition in a subject. Examples of the medical condition can include, but are not limited to dry eye, Meibomian gland dysfunction, goblet cell degranulation, presbyopia, Sjogren's syndrome, pain, ocular pain, corneal pain, facial pain, atypical facial pain, neuralgia, facial neuralgia, trigeminal neuralgia, ocular neuralgia, autonomic dysfunctions, headache, primary headache, secondary headache, myasthenia gravis, intravitreal injection pain and/or side effects, contact lens over wear, contact lens keratopathy, contact lens intolerance, ocular hypertension, loose skin, skin redness, lip ptosis, and/or winkles. The method can include the steps of: delivering a microstimulator into an anatomical structure of the subject innervated by one or more nerves; establishing a capacitive link between the microstimulator and an external electronic device; using the external electronic device to deliver a power signal to the microstimulator; and delivering a therapy signal to a target portion of the anatomical structure via the microstimulator based on the power signal.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
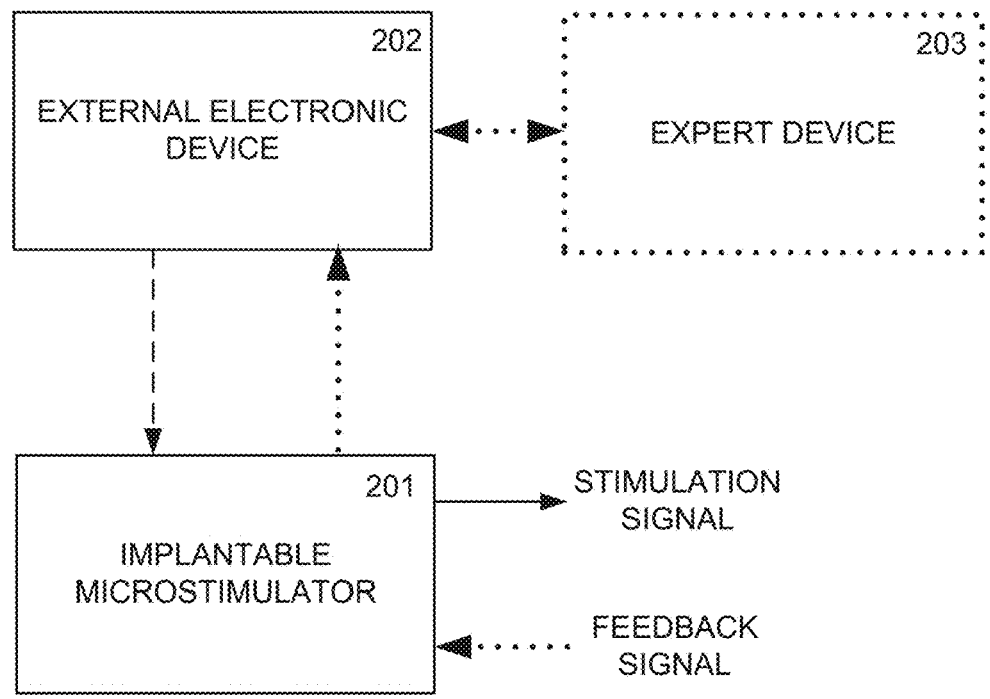
FIG. 1 illustrates a neural modulation system in accordance with an aspect of the present disclosure.

To facilitate understanding of this disclosure, a number of terms are defined below. Terms defined herein have meanings as commonly understood by a person of ordinary skill in the art in the areas relevant to this disclosure.

Terms such as "a," "an" and "the" are not intended to refer only to the singular entity, but can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "medical condition" can refer to an ocular, orbital, autoimmune, and/or neurological disease, disorder, and/or condition.

As used herein, the term "ocular" can refer to something of, for, or like the eye. An ocular disorder can be, for example, dry eye. In order to restore ocular health to a patient with dry eye, a physiology normal amount, level, and/or degree of tears in the eye can be restored and/or maintained to minimize and/or alleviate dryness. Such minimization and/or alleviation of dryness may treat or prevent at least one symptom associated with dry eye disease, such as stinging, burning, and/or scratchy sensation in the eyes; stringy mucus in or around an eye; increased eye irritation from smoke or wind; eye fatigue; eye sensitivity to light; eye redness; a sensation of having something in the eye; difficulty wearing contact lenses; periods of excessive tearing; and blurred vision, often worsening at the end of the day or after focusing for a prolonged period.

As used herein, the terms "tear drainage system", "nasolacrimal drainage system", and "lacrimal drainage system" can be used interchangeably to refer to any one or more connected anatomical structures having two small openings (e.g., puncta). As an example, the puncta may be located in an upper and/or a lower eyelid, wherein these small openings lead to a small tube (e.g., canaliculus) which, in turn, empties into a lacrimal sac and then into a canal called the nasolacrimal duct. It will be understood that the term "drainage system" also may be used interchangeably with "tear drainage system", "nasolacrimal drainage system", and "lacrimal drainage system".

As used herein, the term "medical device" can refer to any objected that is designed to be placed or implanted partially or wholly within a patient's body and/or a naturally occurring orifice of the patient's body for one or more therapeutic or prophylactic purposes. Examples of such therapeutic or prophylactic purposes can include: tissue augmentation, tissue stimulation, contouring, restoring physiological function, repairing and/or restoring tissues damaged by disease or trauma, and/or delivering therapeutic agents to normal, damaged, and/or diseased organs and tissues. While medical devices are often composed of biologically compatible synthetic materials (e.g., medical-grade stainless steel, nitinol, titanium, and/or other metals; exogenous polymers, such as polyurethane, silicone, FLA, PLGA, PGA, PCL, etc.), other materials also may be used in the construction of the medical implant. While not limiting the present disclosure to any particular device, specific medical devices and implants that are particularly relevant to this disclosure include stents, punctal plugs, Crawford tubes, catheters, lacrimal tubes, ocular or other shunts. In some examples, the device may incorporate a contrast material and/or opaque material(s) that may allow for visualization with standard imaging devices (for example, barium to allow for x-ray visualization). In some instances, the medical device can be an implantable device, such as: a neurostimulator, a microstimulator, a device configured to monitor a physiological response of the patient's tissue, a therapeutic agent delivery device, a bone graft, and a sensor. In other instances, the medical device can be a removable device, such as a surgical instrument. As used herein, the terms "medical device", "implant", "device", "medical implant", "implant/device", and the like can be used interchangeably.

As used herein, the term "implanted" can refer to a state in which at least a portion of a device (such as a medical device) is placed or inserted within a host and/or a naturally occurring orifice of the host. In some instances, a medical device can be completely placed or implanted within the host. However, in other instances, some of the medical device can reach or extend to the outside of the host. When a device is referred to as being "implantable", the device can be capable of being implanted within the host.

As used herein, the term "proximal" can refer to a location situation and/or positioned toward a point of origin (e.g., between a medical professional and an implantable microstimulator). In other words, the term "proximal" may refer to a position relatively close to the exterior of the body of a patient and/or closer to a medical professional.

As used herein, the term "distal" can refer to a location situation and/or position away from a point of origin (e.g., behind a lacrimal implant device relative to a physician). In other words, the term "distal" may refer to a position relatively further away from the exterior of the body of a patient and/or further away from a medical processional.

As used herein, the terms "prevention" and/or "preventing" can refer to preventing or slowing development of a disease or disorder in a patient.

As used herein, the terms "treat", "treating", and/or "treatment" can refer to the act of reducing and/or eliminating symptoms of a disease or disorder to improve a condition of a patient to some degree, delaying progression of the disease or disorder, or providing some other effect related to the disease or disorder.

As used herein, the terms "therapeutically effective amount" and/or "pharmaceutically effective amount" can refer to an amount which, when administered to a patient for treating a disease or disorder, will effect such treatment for the disease or disorder.

As used herein, the terms "therapy signal" and "stimulation signal" can refer to an electrical signal designed for neuromodulation. The stimulation signal can be delivered to a patient's tissue of interest for neuromodulation (e.g., stimulation).

As used herein, the term "feedback signal" can refer to a signal provided in response to application of the therapy signal for neuromodulation.

As used herein, the term "medical professional" can refer to any person involved the conducting a procedure involving a medical device including, but not limited to, physicians, medical students, nurse practitioners, nurses, operators, and other staff.

As used herein, the term "patient" can refer to any living or non-living warm-blooded organism including, but not limited to, a human being, a pig, a rat, a mouse, a dog, a cat, a goat, a sheep, a horse, a monkey, an ape, a rabbit, a cow, etc. Non-limiting examples of human subjects are adults, juveniles, infants, and fetuses. The terms "patient" and "subject" can be used interchangeably herein.

As used herein, the term "coupled" and/or "coupling" can refer to the pairing of two objects. The coupling can be wireless, but, in other instances, the coupling can be wired or a combination of wired and wireless. The coupling can facilitate the exchange of current between the two objects and may be, for example, capacitive, resistive, inductive, or the like.

As used herein, the term "biomaterial" can refer to any substance (other than a drug or pharmaceutical) or combination of substances, synthetic or natural in origin, which can be used for any period of time as a hole or as a part of a system that treats, augments, or replaces any cell, tissue, organ, and/or function of the body.

As used herein, the term "biocompatibility" can refer to the ability of a material, such as a biomaterial, to perform a specific application with an appropriate host response.

As used herein, the term "dielectric medium" can refer to a substance, medium, ir bidy that can sustain an electrical field therewithin.

II. Overview

The present disclosure relates generally to systems and methods for preventing, diagnosing, and/or treating one or more medical conditions. The medical condition can be an ocular, orbital, autoimmune, and/or neurological disease, disorder, and/or condition. As an example, the systems and methods of the present disclosure can be used to induce tear production via neuromodulation to treat or prevent dry eye disease. Although the induction of tear production is an example use of the present disclosure, it will be understood that the present disclosure is not limited to induction of treat production. Instead, the present disclosure is related to preventing, diagnosing, and/or treating one or more ocular, orbital, autoimmune, and/or neurological diseases, disorders, and/or conditions. Diseases that can be prevented, diagnosed, and/or treated can include, but are not limited to, dry eye, Meibomian gland dysfunction, goblet cell degranulation, presbyopia, Sjogren's syndrome, pain, ocular pain, corneal pain, facial pain, atypical facial pain, neuralgia, facial neuralgia, trigeminal neuralgia, ocular neuralgia, autonomic dysfunctions, headache, primary headache, secondary headache, myasthenia gravis, intravitreal injection pain and/or side effects, and/or glaucoma. As another example, disorders that can be prevented, diagnosed, and/or treated can include, but is not limited to, contact lens over wear, contact lens keratopathy, contact lens intolerance, and/or ocular hypertension. Conditions that can be prevented, diagnosed, and/or treated can include, but are not limited to, loose skin, skin redness, lip ptosis, and/or winkles.

More specifically, the present disclosure relates to systems and methods employing neuromodulation to prevent, diagnose, and/or treat one or more medical conditions. The neuromodulation can be achieved via application of an electrical signal to an anatomical structure. As an example, when the medical condition is dry eye disease, the anatomical structure can include at least a portion of the nasolacrimal drainage system, so that one or more nerves within the portion of the nasolacrimal drainage system can be neuromodulated to produce bilateral or unilateral lacrimation. The electrical signal can be delivered to the anatomical structure by a microstimulator. The microstimulator can be placed or inserted within the anatomical structure and wirelessly coupled to an external electronic device. For example, the microstimulator can be capacitively coupled to the external electronic device with the patient's skin acting as a dielectric medium. As such, the microstimulator can receive a power signal from the external electronic device.

III. Systems

One aspect of the present disclosure can include a neuromodulation system. The neuromodulation system can deliver a therapy signal to a target anatomical area to prevent, diagnose, and/or treat one or more medical conditions. The therapy signal can be, for example, a stimulation signal configured to stimulate a portion of the target anatomical area to prevent, diagnose, and/or treat one or more medical conditions. The medical condition can be an ocular, orbital, autoimmune, and/or neurological disease, disorder, and/or condition. Diseases that can be prevented, diagnosed, and/or treated can include, but are not limited to, dry eye, Meibomian gland dysfunction, goblet cell degranulation, presbyopia, Sjogren's syndrome, pain, ocular pain, corneal pain, facial pain, atypical facial pain, neuralgia, facial neuralgia, trigeminal neuralgia, ocular neuralgia, autonomic dysfunctions, headache, primary headache, secondary headache, myasthenia gravis, intravitreal injection side effects, and/or glaucoma. As another example, disorders that can be prevented, diagnosed, and/or treated can include, but are not limited to, contact lens over wear, contact lens keratopathy, contact lens intolerance, and/or ocular hypertension. Conditions that can be prevented, diagnosed, and/or treated can include, but are not limited to, loose skin, skin redness, lip ptosis, and/or winkles.

The neuromodulation system can include an implantable microstimulator 201 and an external electronic device 202. The implantable microstimulator 201 can be configured to deliver the therapy signal to the anatomical structure. The implantable microstimulator 201 can be configured for insertion into an anatomical structure of a subject. At least a portion of the implantable microstimulator 201 configured to contact the anatomical structure can be formed of one or more biocompatible materials. The implantable microstimulator 201 can be shaped and sized to correspond to the specific anatomical structure. The anatomical structure can be chosen based on the presence of a particular target nerve or nerves. The target nerve, upon activation, can cause the occurrence of a physiologic function. As an example, the target nerve can be part of a neurological reflex.

The implantable microstimulator 201 can have the capability to deliver a stimulation signal (or therapy signal) to the target nerve or nerves within the anatomical structure to induce a physiologic function. The stimulation signal can be an electrical signal, such as a direct current signal, an alternating current signal, or the like, and can be configured as a charge balanced symmetric or asymmetric biphasic waveform, a charge imbalanced asymmetric biphasic waveform, and/or a monophasic waveform depending on the application. The implantable microstimulator 201 can also provide additional functionality in addition to delivering the stimulation signal. As one example, the implantable microstimulator 201 can have the ability to facilitate drainage of one or more fluids inside the anatomical structure. As another example, the implantable microstimulator 201 can be capable of eluding a drug or other pharmaceutical substance into the anatomical structure. In a further example, the implantable microstimulator 201 can provide feedback related to application of the stimulation signal.

In some instances, the implantable microstimulator 201 can be activated, powered, and/or controlled by the external electronic device 202. The microstimulator 201, in an example, can be operable as a slave device to the master external electronic device 201. However, in other examples, the microstimulator 201 and the external electronic device 202 can be components of a closed loop control system, where the implantable microstimulator 201 provides the additional functionality of recording feedback information from the anatomical structure and sending the feedback information back to the external electronic device 202. The external electronic device can send the feedback information to an external expert device 203 for further analysis.

In either example, the external electronic device 202 can be configured to generate a power transfer waveform (or power signal) that is sent to the implantable microstimulator 201 to activate, power, and/or control the implantable microstimulator 201. The implantable microstimulator 201 may not include a dedicated power source, like a battery, and, instead, may rely on the power signal for activation, power, and/or control. In some instances, the external electronic device 202 can pair the power transfer waveform with a carrier waveform. For example, the carrier waveform can be transposed on top of the power transfer waveform and may be used for data transmission and/or control functions.

Figure 2:
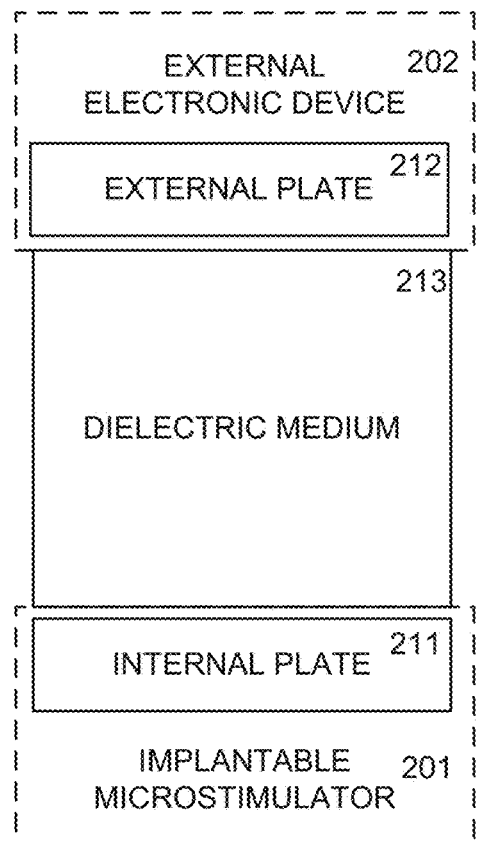
FIG. 2 illustrates a capacitive coupling between the implantable microstimulator and the external electronic device of FIG. 1 established across a dielectric medium.

The implantable microstimulator 201 can be electronically coupled to the external electronic device 202 to exchange the power signal and/or a feedback signal. The electronic coupling can be a wired coupling and/or a wireless coupling. One example of a wireless coupling between the external electronic device 202 and the implantable microstimulator 201 is a capacitive coupling, as shown in FIG. 2. Although capacitive coupling is the example of wireless coupling described in more detail herein, it will be understood that the wireless coupling may be an antenna coupling, an inductive coupling, a resonant inductive coupling, a resistive coupling, an optical coupling, or the like. It will be understood that the implantable microstimulator 201 may include circuitry necessary to be activated, powered, and/or controlled from the external electronic device 202 according to the type of coupling.

Using the capacitive coupling of FIG. 2, the external electronic device 202 and the implantable microstimulator 201 can achieve capacitive power transfer. Both the external electronic device 202 and the implantable microstimulator 201 are separated by a dielectric medium 213 (or dielectric medium), so that the external electronic device 202 and the implantable microstimulator 201 are on either side of the dielectric medium 213. The dielectric medium 213 can be, for example, at least a portion of a subject's body. For example, the portion of the subject's body can include skin. Although the external electronic device 202 and the implantable microstimulator 201 are both illustrated as contacting the dielectric medium 213, it will be understood that one or both of the external electronic device 202 and the implantable microstimulator 201 need not contact the dielectric medium 213 and may be separated from the dielectric medium 213 by a distance less than or equal to a threshold value. The threshold value can depend on the use and orientation of the implantable microstimulator 201.

The external electronic device 202 can include an external plate 212, while the implantable microstimulator 201 can include an internal plate 211. When the external plate 212 and the internal plate 211 are aligned across the dielectric medium 213 (e.g., each plate 211, 212 being in parallel to the dielectric medium 213), the capacitive coupling is created. The "external plate" and the "internal plate" need not be plates per se. Instead, term "plate" is used to mean "portion" or "component", which may be of a length, width, and/or diameter limited only by the length, width, and/or diameter of the implantable microstimulator 201. Capacitive power transfer can occur when the voltage of either the external plate 212 or the internal plate 211 is varied. The configuration of the overall capacitance, surface area of the capacitive plates 211, 212, distance between the plates 211, 212, dielectric medium 213 separating the plates 211, 212, and/or the voltage of the power signal is deterministic for the amount and efficiency of the capacitive power transfer. Compared to traditional capacitive power transfer, the capacitive power transfer of FIG. 2 has a reduced complexity by varying the voltage at just one of the external plate 212 or the internal plate 211.

Figure 3:
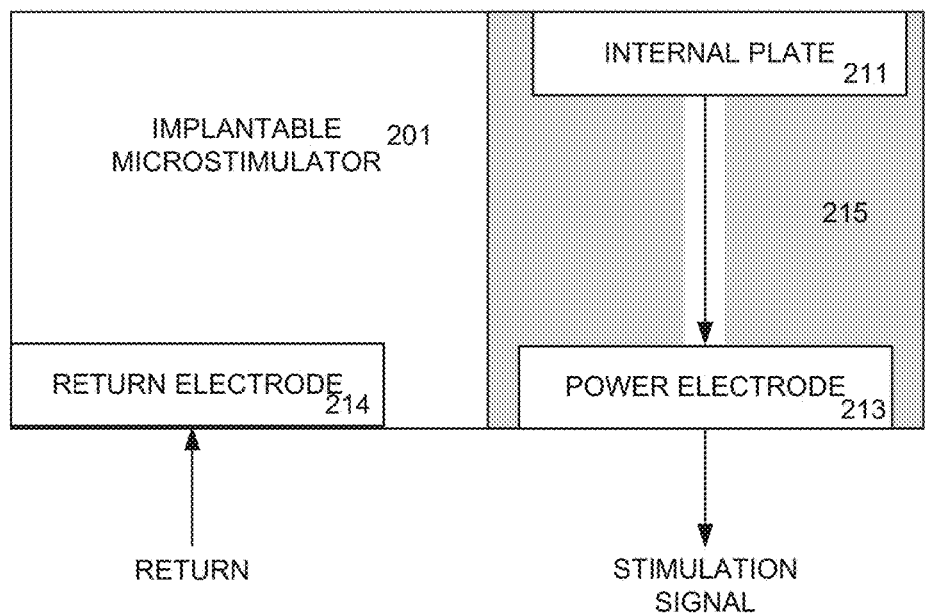
FIG. 3 illustrates an example configuration of the implantable microstimulator of FIG. 1.

FIG. 3 shows an example of the capacitive power transfer within the implantable microstimulator 201. The capacitive power transfer can occur using the external plate 212 and the internal plate 211, with a reference electrode located on the external electronic device 202 and another reference electrode located in the microstimulator 201 (represented as return electrode 214). Stimulation occurs via a power electrode 213 and the return electrode 214. The power electrode 213 is connected to the internal plate 211 so the power signal is converted to the stimulation signal directly. In some instances, the implantable microstimulator 201 may include additional components between the internal plate 211 and the power electrode 213 to facilitate the conversion of the power signal to the stimulation signal.

The internal plate 212 is used in the transfer of power from the external electronic device 202 to the implantable microstimulator 201, the power electrode 213 delivers the stimulation signal to the tissue of interest (the stimulation signal is based on the power received from the external electronic device 202), while the return electrode 214 acts as a passive return reference, establishing a common ground between the implantable microstimulator 201 and the external electronic device 202. The internal plate 211 of the microstimulator 201 can be electrically connected to the power electrode 213, but electrically isolated 215 from the return electrode 214. The power electrode 213 can also be electrically isolated 215 from the return electrode 214, but connected to the subject's body to deliver the stimulation signal. It should be noted that the components of the implantable microstimulator 201 are not drawn to scale. In some examples, the internal plate 211 can extend along the entirety of the implantable microstimulator 201. In other examples, the insulation 215 can be more extensive or less extensive than shown. Additionally, the power electrode 213 and the return electrode 214 can be arranged in a different manner than shown.

As an example, the implantable microstimulator 201 can include a flex circuit or other means to establish an internal capacitor between the internal plate 211/power electrode 213 and the return electrode 214. Advantageously, in this example, the implantable microstimulator 201 need not include any active or passive circuit elements within the implantable microstimulator 201.

The external electronic device 202, shown in FIG. 1, can be operated by a medical professional and/or by the subject in need of the neuromodulation. In instances where the subject operates the external electronic device 202, the external electronic device 202 can be designed in a manner that is easy for the subject to use, such as in a form that is attachable to the subject's skin, in a form capable of being held or placed against the subject's skin, worn by the patient, or the like. For example, the external electronic device 202 can be embodied in a form that is familiar to the subject, such as a key fob, a pen-like cylinder, a sleep mask, pair of glasses, a nose clip, a flexible bandage, virtual reality (VR) goggles, or the like. Regardless of form, the external electronic device 202 includes all elements necessary to generate the power signal and/or the carrier signal, and other electronics to power, control and/or manipulate the microstimulator 201. For example, the elements included with the external electronic device 202 can include a power source to deliver the power signal and/or the carrier signal. As another example, the elements included with the external electronic device 202 can include a controller to control delivery of the power signal. The power source and the controller can be enclosed within a casing. Additionally, the casing can also include at least a portion configured to contact the subject's skin that includes an electrically conductive material, which can be at least partially biocompatible. Additionally, one electrically conductive device 202 can have the capabilities to interface with and communicate with one or more microstimulators 201. However, in some instances, one electrically conductive device 202 can have the capabilities to interface with and communicate with two or more microstimulators 201 so that each of the microstimulators 201 can apply the therapy signal when signaled to do so.

In some instances, the electrically conductive material can be placed in communication with the microstimulator 201 in a unilateral manner, but in other instances, the electrically conductive material can be placed in communication with the microstimulator 201 in a bilateral manner. The unilateral or bilateral nature of capacitive power transfer can be controlled individually.

Moreover, the external electronic device 201 can include a mechanism to allow the subject to control the amount and duration of the stimulation, such as one or more input buttons that allow the subject to control stimulation amplitude, pulse width, frequency, and/or stimulation duration or other aspects of the stimulation. The external electronic device 202, in some instances, can include one or more input buttons that allow for user control of the stimulation parameters. In other instances, the external electronic device 202 can have an onboard memory to store data related to use of the system, including stimulation parameters, duration, power efficiencies, biofeedback signals, subject input, and the like. For example, the external electronic device 202 can include the ability to store data relative to the subject's medical condition via sensors within the microstimulator 201, via sensors on the external electronic device 202, or via input from the subject (e.g., in an application that is linked via Bluetooth or other wireless communication mechanism to the external electronic device 202). The data that is collected can be used to create closed loop therapies, provide relative health data to a medical professional, track personal health related information, saved for future therapy improvements or innovations (e.g., stored as "big data"), or the like. The stored data can be used, for example, to alert a medical provider when the microstimulator 201 may need to be replaced or feedback regarding the medical condition, to alert the subject when the medical condition occurs, to determine when the stimulation should be delivered, etc.

In some instances, the external electronic device 202 can include a feedback system to provide feedback to the subject. The feedback provided to the subject can be a visual feedback, an audio feedback, a touch/pressure/vibration feedback, or the like. The feedback system can be used to guide placement of the external electronic device 202 to establish the capacitive link with the implantable microstimulator 201. The feedback system may also provide alerts to the subject during therapy. For example, the alerts can be provided when 50% of the max amplitude has been reached, 100% of the max amplitude has been reached, the duration of the stimulation is 50% complete, the duration of the stimulation is 100% complete, the position of the external electronic device 202 has been moved and needs to be realigned, or the like.

In other instances, the external electronic device 202 can automatically control therapy. The subject can use the feedback system to place the external electronic device 202 correctly, and the external electronic device 202 can automatically ramp up the therapy signal until the therapy signal reaches a pre-determined level that is known to be comfortable and effective for the subject. The external electronic device 202 can receive biofeedback to control delivery of the therapy signal. For example, the external electronic device 202 can include or interface with a camera, a Doppler system, or other type of sensor to provide biofeedback signals.

In some instances, the external electronic device 202 can include a communication mechanism to communicate with an external expert device 203 and/or to communicate with the microstimulator 201. The external electronic device 202, in some instances, can receive control and power parameters from the external expert device 203 according to a wired connection and/or a wireless connection. For example, the communication mechanism can include a Bluetooth communication mechanism or other type of wireless communication mechanism.

The expert device 203 can be associated with a medical professional to communicate with the external electronic device 202 to adjust stimulation parameters associated with the microstimulator 201 and/or to assess functionality of the microstimulator 201. Alternatively, the expert device 203 can include a mobile application that can interact with the external electronic device 202 and a device associated with a medical professional. As another example, the expert device 203 can be a cloud-based server.

In another instance, the expert device 203 can interface with and/or include a physician programmer. The physician programmer can be configured as a tablet, a personal computer, a smartphone appliance, a tablet application or other suitable means. The physician programmer allows the physician to modulate the therapy for each subject. The physician programmer is configured to allow the physician to input, save, store and recall information about a specific subject's therapy into/from a secure database. As an example, the physician programmer can establish different therapy levels for the subject (e.g., the first instance of a therapeutic effect, the highest level tolerated by the subject, etc.), and the subject can choose from the different therapy levels for each application of the therapy. The physician programmer can also determine the effectiveness of the capacitive link, the power transfer efficiency, and the like. As such, the physician programmer can determine the optimum placement of the external conductive pads by providing real time feedback regarding the capacitive link.

An example use of the neuromodulation system of FIG. 1 is inducing tear production to treat or prevent dry eye disease. A description of dry eye disease is provided in U.S. patent application Ser. No. 15/180,451, which is incorporated herein by reference. Tears are produced via unilateral or bilateral reflex lacrimation, which can be induced via neuromodulation of one or more nerves that innervate the punctum and/or canaliculus of the nasolacrimal drainage system. Similarly, a description of tear production is provided in U.S. patent application Ser. No. 15/180,451, which is incorporated herein by reference.

Figure 4:
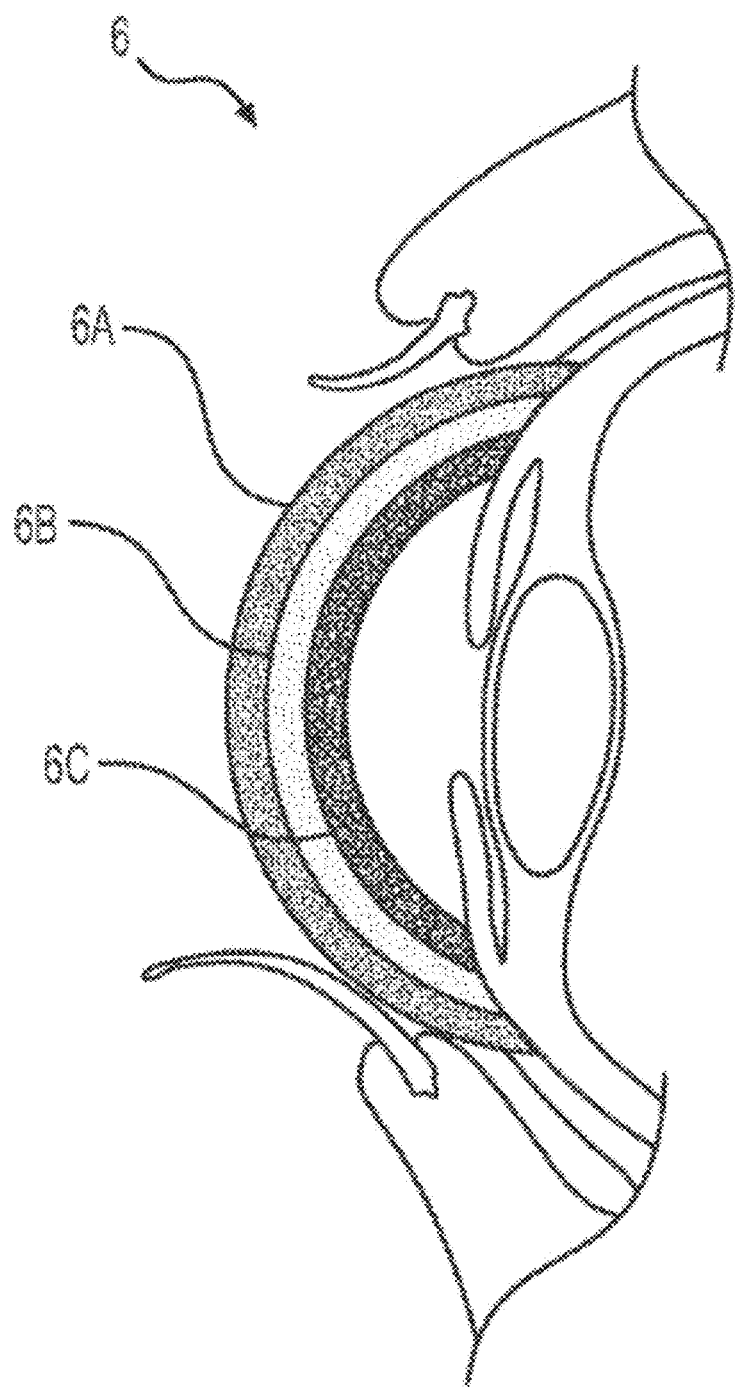
FIG. 4 illustrates a side-view of an eye of a subject, depicting the three layers of naturally produced tears.
Figure 5:
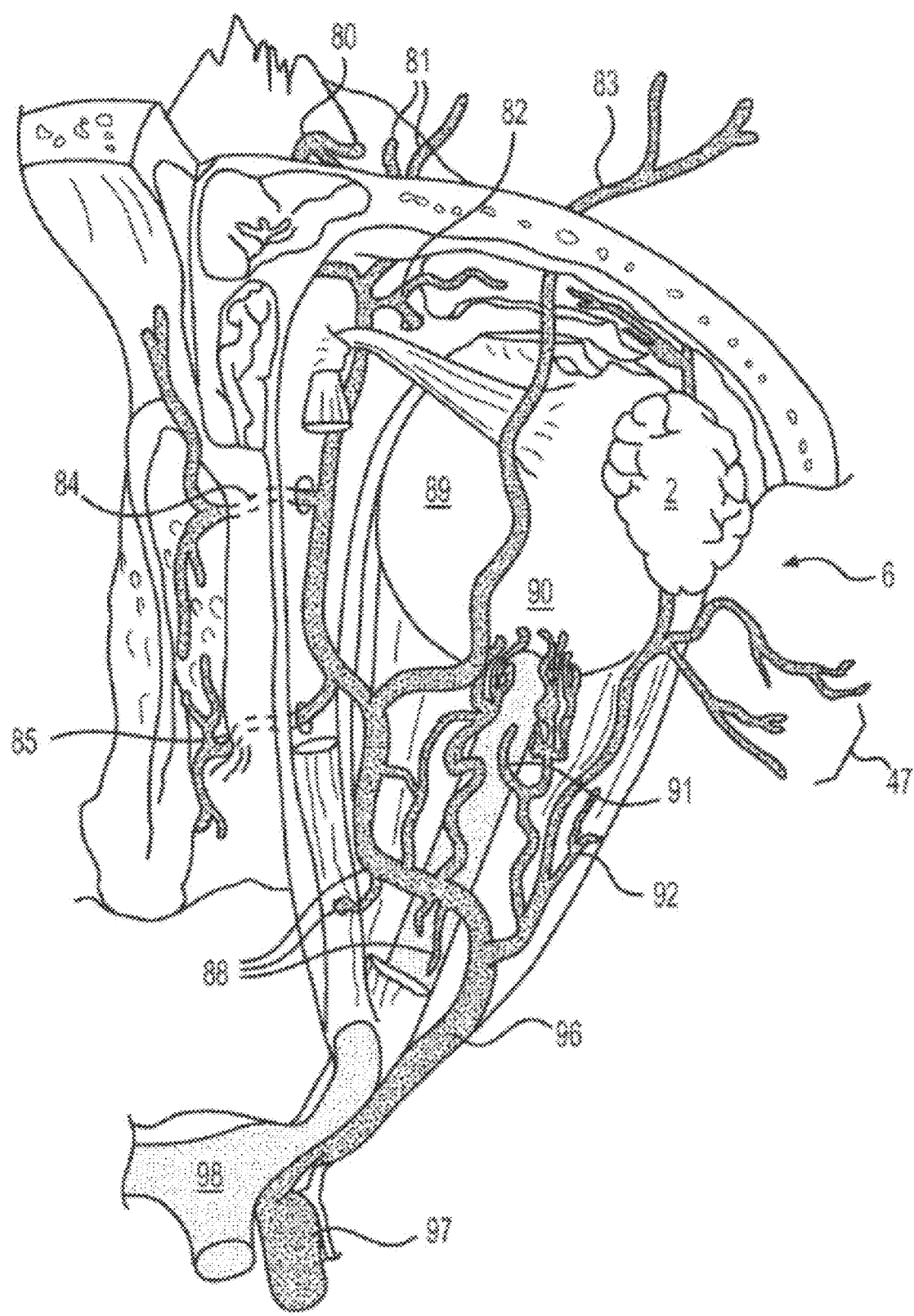
FIG. 5 illustrates anatomical features of nerves and blood vessels related to the eye and lacrimal system of a subject.
Figure 6:
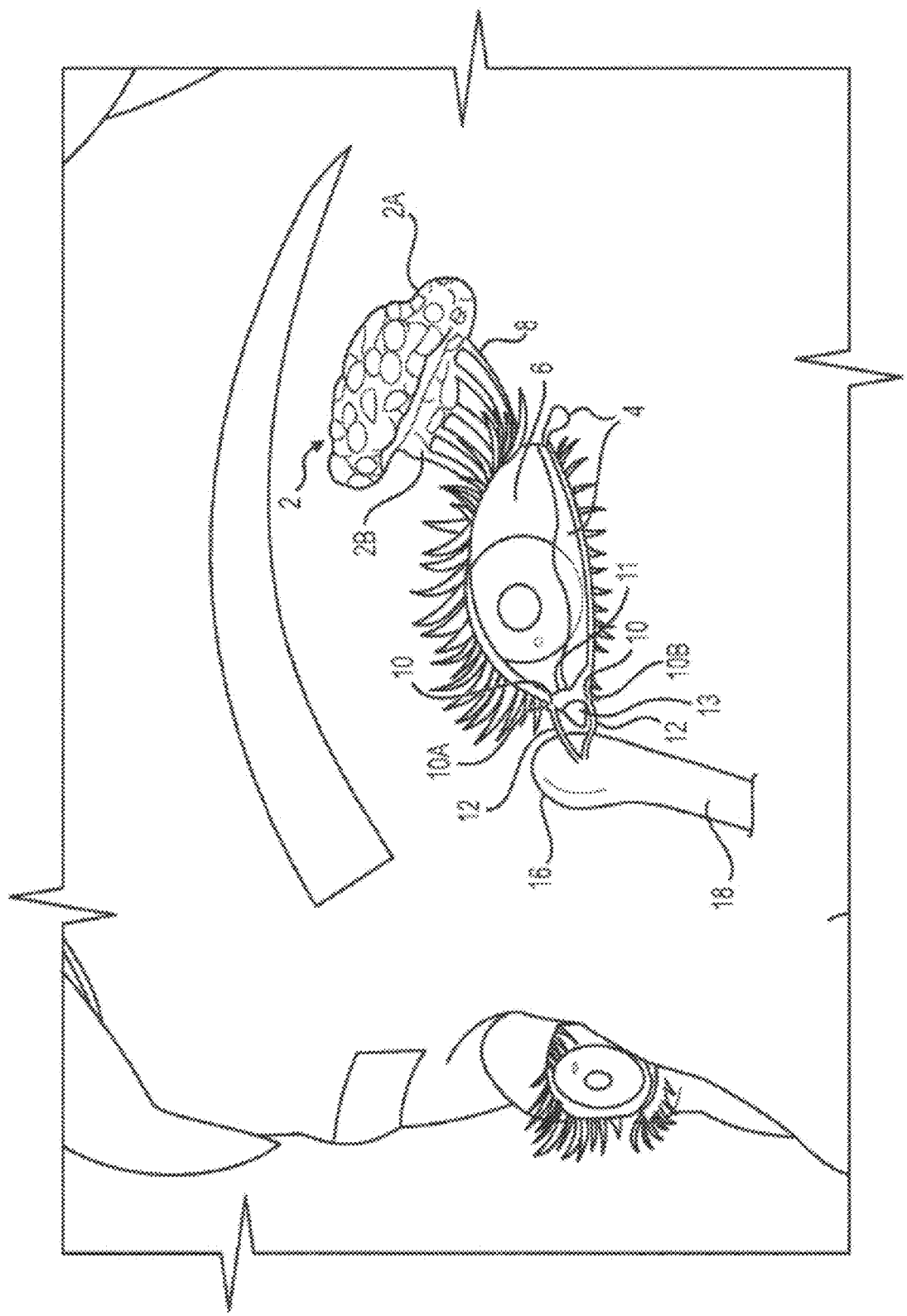
FIG. 6 illustrates anatomical features related to the eye and lacrimal system of a subject.

A general depiction of physiology of an eye of a subject is shown in FIGS. 4-6. However, U.S. patent application Ser. No. 15/180,451 provides a more detailed description of the physiology of the subject's eye.

FIG. 4 illustrates a side view of an eye 6 of a subject, including three layers of naturally produced tears. For example, as shown in FIG. 4, naturally produced tears include an outer oily layer 6A, a middle watery layer (or aqueous layer) 6B, and an inner mucus layer 6C, which is spread across the surface of the eye (the ocular surface) whenever the subject blinks, thereby providing lubrication, washing away foreign matter, reducing the risk of infection, and keeping the surface of the eye 6 smooth and clear.

FIG. 5 illustrates anatomical features of nerves and blood vessels related to the eye 6 and the lacrimal system of a subject. Such nerves and blood vessels include the dorsal nasal vessel 80, the frontal 81, the medial palpebral 82, the supraorbital 83, the anterior ethmoidal 84, the posterior ethmoidal 85, the muscular 88, the bulb of the eye 89, the ciliary 90, the arteria centralis retinae 91, the lacrimal 92, the zygomatic branches 94, the ophthalmic 96, the internal carotid 97, the lacrimal gland 2, and the optic nerve 98.

FIG. 6 illustrates additional anatomical features related to the lacrimal system of the eye 6 of a subject. As shown, the lacrimal gland 2 is positioned in the upper outer portion of the orbit of each eye 6. The lacrimal gland 2 includes the orbital (superior) portion 2A and the palpebral (inferior) portion 2B. The lacrimal gland 2 secretes the aqueous layer 6B of tears 4, which are delivered from the lacrimal gland 2 to the surface of the eye 6 via one or more channels or ducts 8 of the lacrimal gland 2. Tears 4 drain from the eye 6, towards a plica semilunaris 11 and lacrimal caruncle 13 via the nasolacrimal drainage system, which includes two puncta 10 located on a lacrimal papilla (e.g., superior lacrimal papilla 10A or inferior lacrimal papilla 10B). Each puncta 10 includes a minute orifice or opening in fluid communication with canaliculi 12. The canaliculi 12 converge and drain into the lacrimal sac 16, which in turn, is in fluid communication with the nasolacrimal duct 18.

Figure 7:
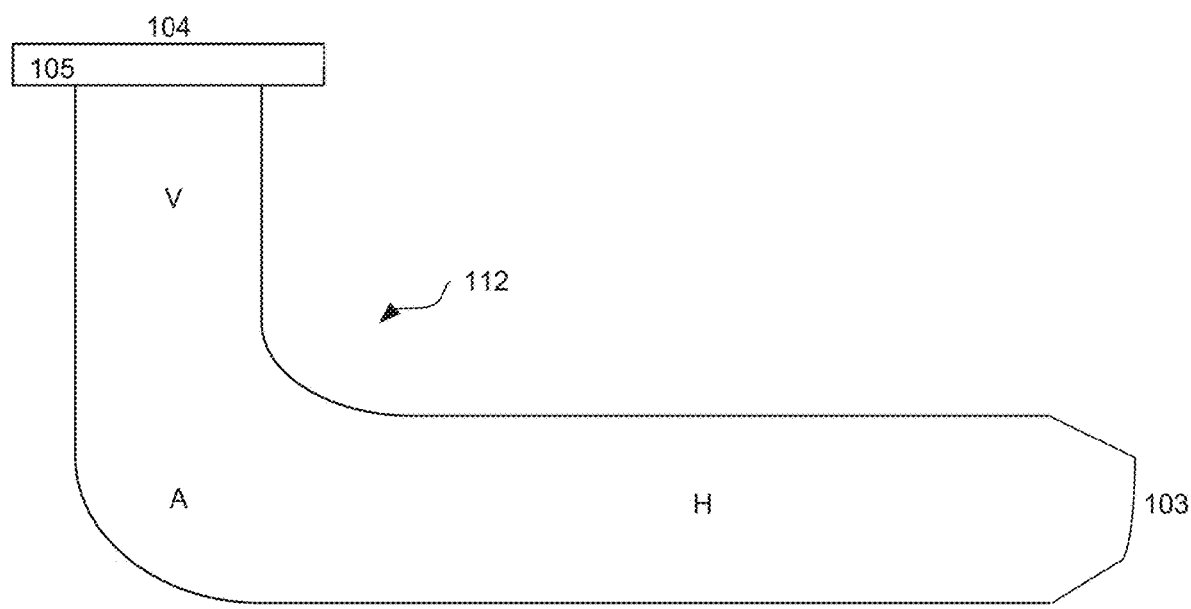
FIG. 7 illustrates an example structure of the microstimulator of FIG. 1 implemented for inducing tear production.
Figure 9:
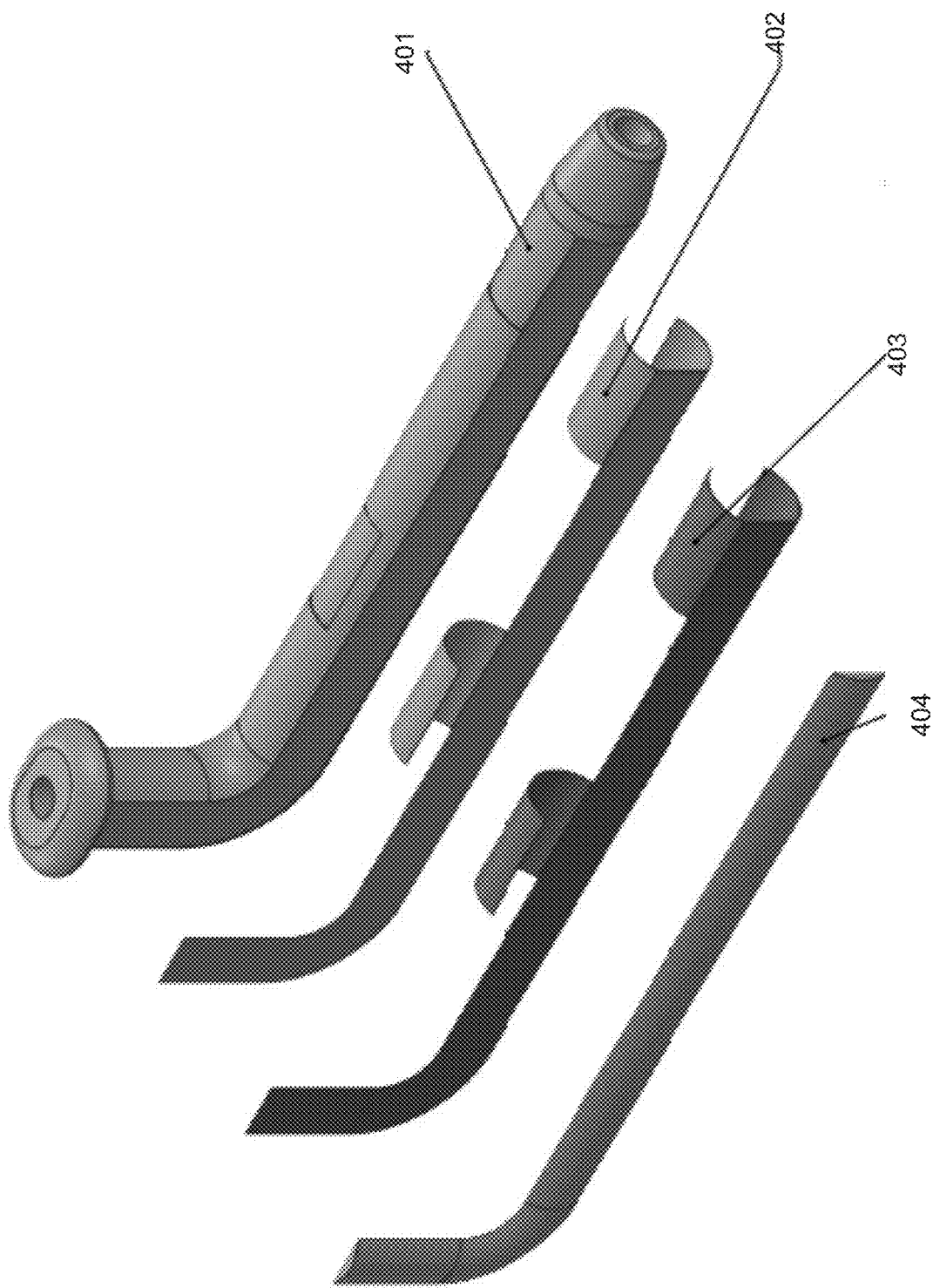
FIG. 9 illustrates another example configuration of the microstimulator of FIG. 7 constructed without the flex circuit.
Figure 11:
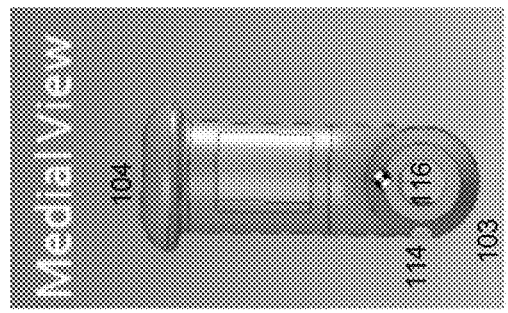
FIGS. 10, 11, and 12 each illustrate different views of the example structure of the microstimulator of FIGS. 8 and 9.
Figure 10:
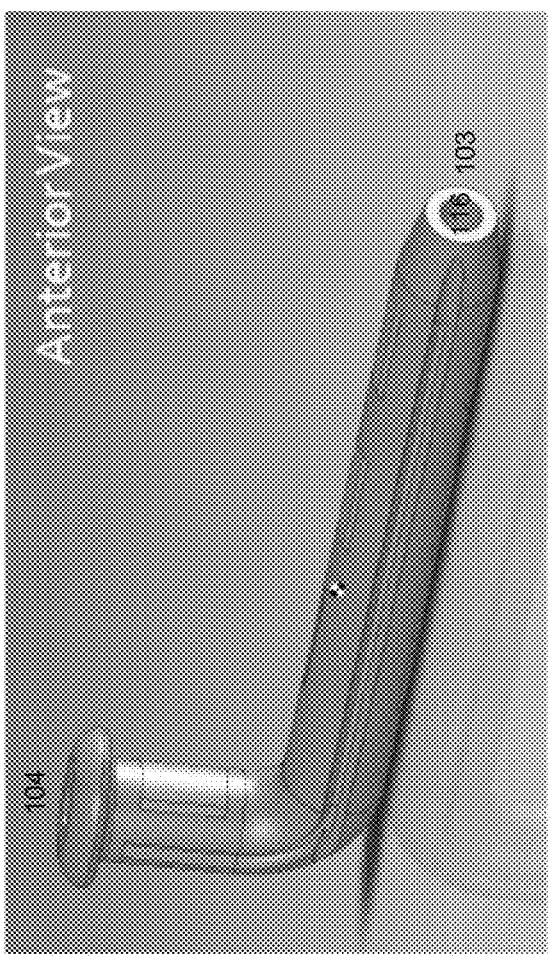
Figure 12:
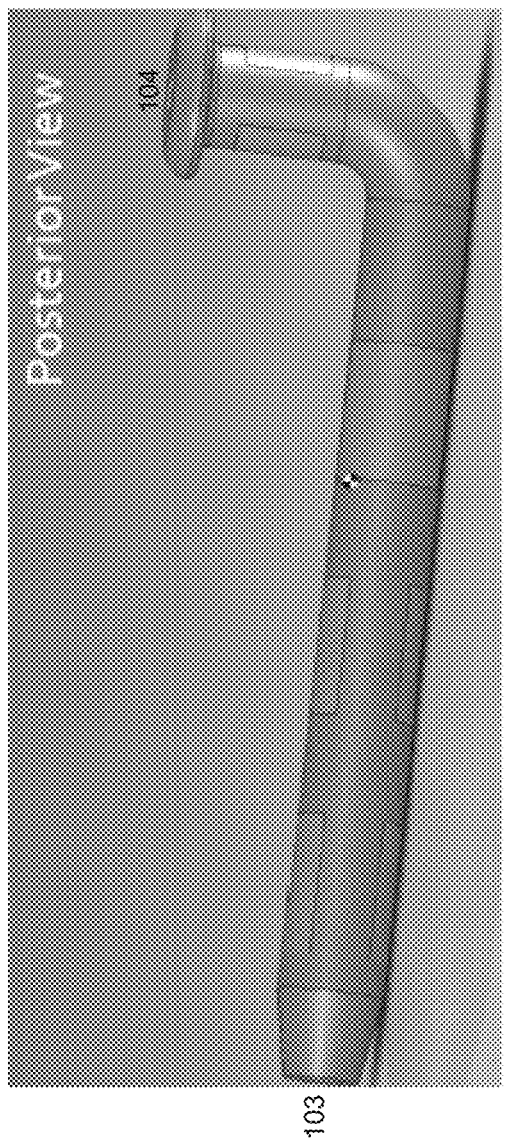

In order to induce tear production, one or more devices (like implantable microstimulator 201, an example of which is shown in FIG. 7 that is configured for the induction of tear production) may be positioned within the nasolacrimal drainage system to prompt or stimulate the lacrimal gland 2. As shown in FIG. 7, the microstimulator has a body 112; an electrically conductive insert (an example of a flex circuit shown in FIG. 8) can be arranged within the body 112 to create the capacitively coupled link with an external electronic device, as described above with regard to FIGS. 1-3. However, an example an equivalent microstimulator without the flex circuit (with the electrically conductive parts deposited on the body 112) is shown in FIG. 9. Additional views of the microstimulator are shown in FIGS. 10-12. FIG. 10 shows an anterior view; FIG. 11 shows a medial view; FIG. 12 shows a posterior view.

At least a portion of the body 112 configured to be implanted within the nasolacrimal drainage system can be formed of one or more biocompatible materials. Biocompatible materials can include certain polymer materials, metal materials, silicone materials, urethane materials, or the like, which do not cause an appreciable immune reaction. Examples of such materials can include, but are not limited to, polyimide, palladium, silicone, and/or urethane.

The body 112 includes a vertical component (V), a horizontal component (H), and a curved portion (A) extending between and connecting the horizontal portion (H) and the vertical portion (V). The curved portion (A) can arrange the horizontal portion (H) and the vertical portion (V) at an angle relative to one another. At least one of the horizontal component (H) and the vertical component (V) can have a cylindrical cross section with a diameter from 0.2 mm to 0.8 mm. However, the horizontal component (H) includes an end portion that is tapered to facilitate implantation of the microstimulator.

The horizontal component (H) can be longer than the vertical component (V). For example, the horizontal component (H) can be between 1 and 8 mm in length, or between 4 and 6 mm in length, while the vertical component (V) can be between 0.1 and 3 mm in length, or between 0.5 and 2 mm in length. Even more specifically, the horizontal component (H) can be between 5 and 6 mm in length, while the vertical component (V) can be between 1.6 and 1.8 mm in length.

The angle between the vertical component (V) and the horizontal component (H) established by the curved portion (A) can be between 70 degrees and 120 degrees. As another example, the angle can be between 90 and 110 degrees. Even more specifically, the angle can be 90 degrees. The angle is specifically chosen to aid in retention of the microstimulator within the punctum and canaliculus. The microstimulator is not anchored by any means within the punctum or canaliculus. The microstimulator shape and angle are selected to enhance the unanchored in vivo retention.

In some instances, a faceplate 105 can cover the vertical component (V) of the body 112. The faceplate can be, in its most general form, a surface that is wider than the vertical component (V). For example, the faceplate 105 may aid in the unanchored in vivo retention based on the associated shape and/or thickness. The faceplate 105 is a cap like structure that is placed on the proximal portion 104 of the microstimulator to prevent internal migration of the microstimulator, ease implantation (e.g., insertion) of the microstimulator, or other functions. The faceplate 105 can cover at least a portion of the body 112. Additionally, the faceplate 105 can include circuitry required to communicate with the external electronic device in a way other than the capacitive coupling, such as a wireless transceiver.

As an example, the faceplate 105 can be positioned on the outer surface of the punctum. The shape of the faceplate 105 can be oval with a long dimension of 0.5 to 2 mm and a short dimension of 0.2 to 1 mm, or, more specifically, 1×0.8 mm (long vs. short axis). The long axis can be orientated lateral to medial when inserted such that the long axis is orientated from the nose to temple. The corresponding thickness of the faceplate 105 can be between 0.1 mm and 0.3 mm, more specifically, 0.2 mm. In instances, the faceplate 105 has an infinity design with the edges of the oval faceplate 105 being rounded to a very thin or infinity edge. The faceplate 105 can also be used to ease the insertion of the microstimulator into the punctum and canaliculus by forceps or other insertion tools. The distal end 103 of the microstimulator can be tapered down to ease insertion, as well.

Since the microstimulator is configured to be inserted into the punctum and the canaliculus and to stimulate the surrounding tissue, the microstimulator may occlude tear drainage. If the microstimulator occludes the tear drainage, this may inadvertently cause the electrical properties of the tissue surrounding the microstimulator to change in a manner that will alter the stimulation characteristics adversely. Specifically, in a dry environment, the tissue impedances will increase and this will cause the stimulation amplitudes needed to achieve the desired result to increase over time. These changes in system impedance may cause changes in how the stimulation is perceived by the subject, the overall effect of stimulation and thus the efficacy of the therapy. To eliminate some of the variable tissue impedances caused by the placement of the microstimulator, the microstimulator may include features that allow for ongoing tear drainage as well as tear fluid to flow over and around the microstimulator while inserted into the punctum and canaliculus.

In one example, the microstimulator may include a central lumen (shown as element 116 in FIGS. 9 and 10) that extends longitudinally. For example, the central lumen can extend between the proximal end 104 and the distal end 103. The central lumen 116 allows for tear drainage. In some instances, the radial channels may allow the tear drainage to coat the mucosa lining of the punctum and canaliculus throughout the length of the microstimulator body 112. The radial channels may be spaced to occur around the circumference of the microstimulator and spaced such that they occur along the entire length of the microstimulator. In one example, the radial channels occur every 2 mm from the faceplate to the end of the microstimulator and, at each 2 mm occurrence, there are two or more channels radially orientated equally around the circumference of the microstimulator. The diameter of the radial channels can be from 0.05 mm to 0.3 mm. The axial lumen and radial channels may be open and allow for free flowing of tears throughout the nasolacrimal system.

In another example, the microstimulator includes the central lumen 116, as well as one or more micro-channels and/or grooves on the outside of the body of the microstimulator. The micro-channels extend from the distal portion of the microstimulator to the proximal portion just below the faceplate 105. Tear fluid can drain from the eye through the lower punctum (through the central lumen 116 in the microstimulator), as well as through the punctum on the upper eyelid. Fluid draining from the upper punctum will also flow in a retrograde manner around the lower canaliculus and surround the microstimulator by flowing through the micro-channels to bath the microstimulator (including at least a portion of the body 112) and surrounding tissue.

In other examples, the central lumen 116, radial channels, micro-channels, and/or faceplate 105 may contain or be impregnated with a material that allows for drug elution into a target site. The faceplate 105, central lumen 116, and/or radial channels may elute a NSAID or other corticosteroids, which will help to reduce inflammation of the surrounding tissue from the insertion of the device and help to promote healing and stable tissue interface after the insertion of the microstimulator. Other drugs can also be eluted that are helpful in dry eye disease or other ocular diseases as well. The drug concentration amounts can be controlled by the amount of tear fluid that is allowed to flow through or around the microstimulator. The drug can be eluted using electrical energy, using iontophoresis methods, in which small microcurrents are used to release and drive the compound or drug in precise areas and/or in precise amounts. Such drug delivery can be done based on a pre-determined schedule, or using biofeedback in a closed loop manner. The biofeedback can include bathing the faceplate 105 in tear fluid in response to delivery of the therapy signal to the target biological site to trigger release of the pharmaceutical. In some instances, the drug delivery can occur through degradation or erosion of a biodegradable or erodible coating (like PLGA or similar co-polymer).

The central lumen 116, in another example, may have a means of measuring the volume or velocity of tears flowing through the microstimulator. For example, the central lumen can have one or more sensors therein to measure a property of fluid flowing therethrough, including volume, velocity, and the like. The volume or velocity of tear flow could be used as a close-loop system, in which the microstimulator alerts the user that the tear production is dropping and that would cause the user to apply the therapy. Such a measurement may be done using a piezoelectric sensor, a bladder diaphragm or using Doppler (ultrasound, laser, optical, etc.).

The microstimulator will communicate (via long range communication, Bluetooth or other suitable means) with a smartphone, smartwatch, or other device that can alert the patients to the need to re-apply therapy. In one example, the closed loop sensor can also be placed in the faceplate and adjacent to the central lumen but situated within the faceplate along with any necessary components (e.g. circuits, etc.,) to allow for proper functionality of the tear sensor. In another embodiment, the sensor may be configured to sense the chemical composition of the tear fluid, sensing the amount of certain proteins or other cellular components that would trigger an additional application of therapy by the patient user. In another embodiment, the microstimulator may use electrode impedances to characterize the amount of tear productions. For example, if the impedances start to increase, this would simulate a decrease in fluid flowing through the nasolacrimal system, and in a closed loop fashion trigger use of the therapy to produce more tears. Long or short-term trending of the impedance values over time can also be used to provide treatment options that are individualized for each patient. If the impedance indicates that the patient's tear production is the lowest during the morning, the system can remind the patient to stimulate at certain times that are associated with the lowest amount of tear production. This can be done through a smartphone app or through an associated wearable smart device or other suitable means of interacting with the subject. In some instances, the stimulation can be automatic as part of a closed loop control system.

Inside the body, the microstimulator can include the electrically conductive plate (like internal plate 213 of FIGS. 2 and 3). The surface area of the electrically conductive plate can be chosen large enough to receive the power signal from the external electronic device strong enough to create the stimulation signal that facilitates tear production. The electrically conductive insert can also include the electrode coupled to the electrically conductive plate (shown in FIG. 3) to deliver the therapy signal to the biological target site in the subject. In some examples, the electrode can be physically connected to the electrically conductive plate. The electrically conductive plate can also include a reference electrode or return electrode (shown in FIG. 3) isolated from the conductive plate to create a reference or return path that is connected to the external electronic device.

Each of the electrodes can be made of an electrically conductive material, like platinum, platinum/iridium, palladium, or another inert metal that is electrically conductive and appropriate for electrical stimulation. The electrodes can be positioned between the distal portion 104 of the microstimulator and the proximal portion 103 of the microstimulator. For example, the electrodes can be positioned such that they are equally spaced longitudinally from the distal portion 104 to the proximal portion 103 of the microstimulator. Each electrode is then radially exposed to the surrounding tissue in a 180-degree orientation. In one example, the electrodes can be quarter moon-shaped so that these electrodes are only exposed in quarter segments on the top and bottom of the microstimulator to avoid any overlap with the internal plate. The overlap is avoided to ensure the capacitance created remains consistent. The rise/fall time (e.g., time constant) of the capacitor created is important in creating the therapy signal waveform. Changes in the capacitance created can change the waveform and waveform efficiency.

In some instances, four electrodes are exposed to the surrounding environment and each electrode is exposed to the environment at two locations around the circumference of the microstimulator body. The exposed portions are between 40 and 180 degrees from each other around the circumference of the microstimulator body. It should be appreciated that the exposed electrodes can be positioned using any orientation around or within the microstimulator body from the distal portion 104 to the proximal portion 103 of the microstimulator body. For example, the orientation can be determined based on the orientation of the microstimulator 201 compared to the external device 202.

In some instances, the microstimulator can be configured such that there is no battery contained within the microstimulator. The microstimulator can be configured to receive power from an external electronic device. In other words, the microstimulator can be a slave to the external electronic device and can deliver stimulation when activated by the external electronic device. The microstimulator and the external electronic device can exchange energy wirelessly, using a capacitive power transfer method, as described above with respect to FIGS. 2 and 3. In these instances, the microstimulator is configured for insertion through the punctum of the lower eyelid into the canaliculus and configured such that the associated "plate" is oriented to be parallel with the external skin overlaying the canaliculus to establish the capacitive link with the external electronic device. The "plate" can be located on a side of the microstimulator and covers the majority of the surface area on the one side of the microstimulator.

Capacitive power transfer is useful for the microstimulator, when the microstimulator requires charge balancing. The external electronic device is responsible for generating the power transfer waveform, which capacitively couples power to the internal device. Additionally, the external electronic device is responsible for generating the carrier waveform, which can be used for data transmission or control of the microstimulator. As such, the external electronic device creates the carrier waveform by a voltage controlled oscillator (VCO), or voltage to frequency converter (VFC). The frequency is set by a digital to analog converter from a microcontroller. This carrier waveform may be buffered by a unity gain configured op-amp, such that the VCO/VFC is not loaded. The buffer waveform is then amplified/attenuated and DC shifted by a second op-amp. The gain of waveform is set by a series of feedback resistors. Alternatively, the feedback resistors can be replaced with analog or digital potentiometers to adjust the gain. In this embodiment, the microcontroller is able to control the gain through digital communication solely. In this embodiment, the carrier waveform is also DC shifted using a second stage. This is done by asserting a DC bias voltage to the op-amp. This DC bias voltage is generated and adjusted using a Digital to Analog Converter on the microcontroller.

The generated output waveform at the power electrode may be biphasic, in which each pulse may include a first phase, an interphase delay, and a second phase. During the first phase, a positive DC bias is applied to the output, with the carrier frequency transposed on top. During this phase, electrical current is induced through a capacitively coupled load. During the interphase delay, the carrier waveform and DC bias are shut off and no waveform is generated. During the second phase, a negative DC bias is applied to the output, with a carrier frequency transposed on top, which induces a current in the opposite direction of the first phase. This phase is used as an active recovery, or charge-balancing phase for stimulation. Between pulses, the carrier waveform and DC bias are shut off, and the output remains off until the next active stimulation phase. This period between pulses also acts as a passive recovery phase, allowing any excess charge to be recaptured.

The power transfer through the capacitive link is generated by the edge transition of the DC bias. The capacitive link between the external and internal device is high impedance at DC, but is low impedance when an AC signal is applied. The actual impedance varies based on the frequency of the signal and the value of the capacitance. In this respect, by applying an increasing/decreasing voltage across the capacitive link, the link acts as a low impedance medium and current is induced. The magnitude of the current is determined by the slew rate of the signal and total capacitance of the link. The rising and falling edges at the beginning of each phase of the waveform generate this induced current at the electrodes on the inserted microstimulator.

In some instances, the capacitive link between the external electronic device and the microstimulator can be through an electrically conductive insert within the body 112. The electrically conductive insert can be a flex circuit configured or formed into a circular cross section. The flex circuit can be positioned between the central lumen 116 and the surface of the body 112 of the microstimulator.

The flex circuit can include the plate, the power electrode, and the return electrode. Similar to FIG. 3, the power electrode is electrically connected to the plate. However, the plate is electrically isolated from the body 112, leaving only the power electrode exposed to the tissue in the anatomical area. The return electrode is isolated from the capacitive plate and the power electrode, but electrically connected to the body 112. When activated by the external electronic device 202, the stimulation waveform can be generated between the power electrode and the return electrode. The resulting electrical field will then activate nerves that innervate the punctum and canalicus, which will then result in reflexive lacrimation. However, the return electrode is not necessarily in the flex circuit; instead, the return electrode can be located on the external electronic device to create a common system ground for the external electronic device and the flex circuit.

The flex circuit can be created in different ways. One example is by sputtering, depositing, or otherwise adhering a biocompatible material to a base substrate. An example of this is shown in element 106A of FIG. 8, where a biocompatible conductive material 107 is adhered to a base substrate 108. As an example, the base substrate 108 can be polyimide (such as a thin polyimide sheet) and the biocompatible conductive material 107 is a metal. As illustrated, the base substrate 108 can be configured into a geometry that can be furled, rolled, or otherwise curled into a circular cross-section. After the biocompatible conductive material 107 is adhered to the base substrate, a third layer is applied to the areas of the flex circuit to be electrically isolated from the subject's body upon insertion. The third layer can be a liquid polyimide (such as a very thin liquid polyimide), for example. The resulting flex circuit 106A is configured into a circular cross-section shown in element 1068. The circular cross section creates the internal capacitor, which allows for energy and/or the stimulation waveform to be transferred or delivered without any internal circuit components. As such, there are no passive circuit elements or active circuit elements within the body 112 and no internal battery.

Figure 8:
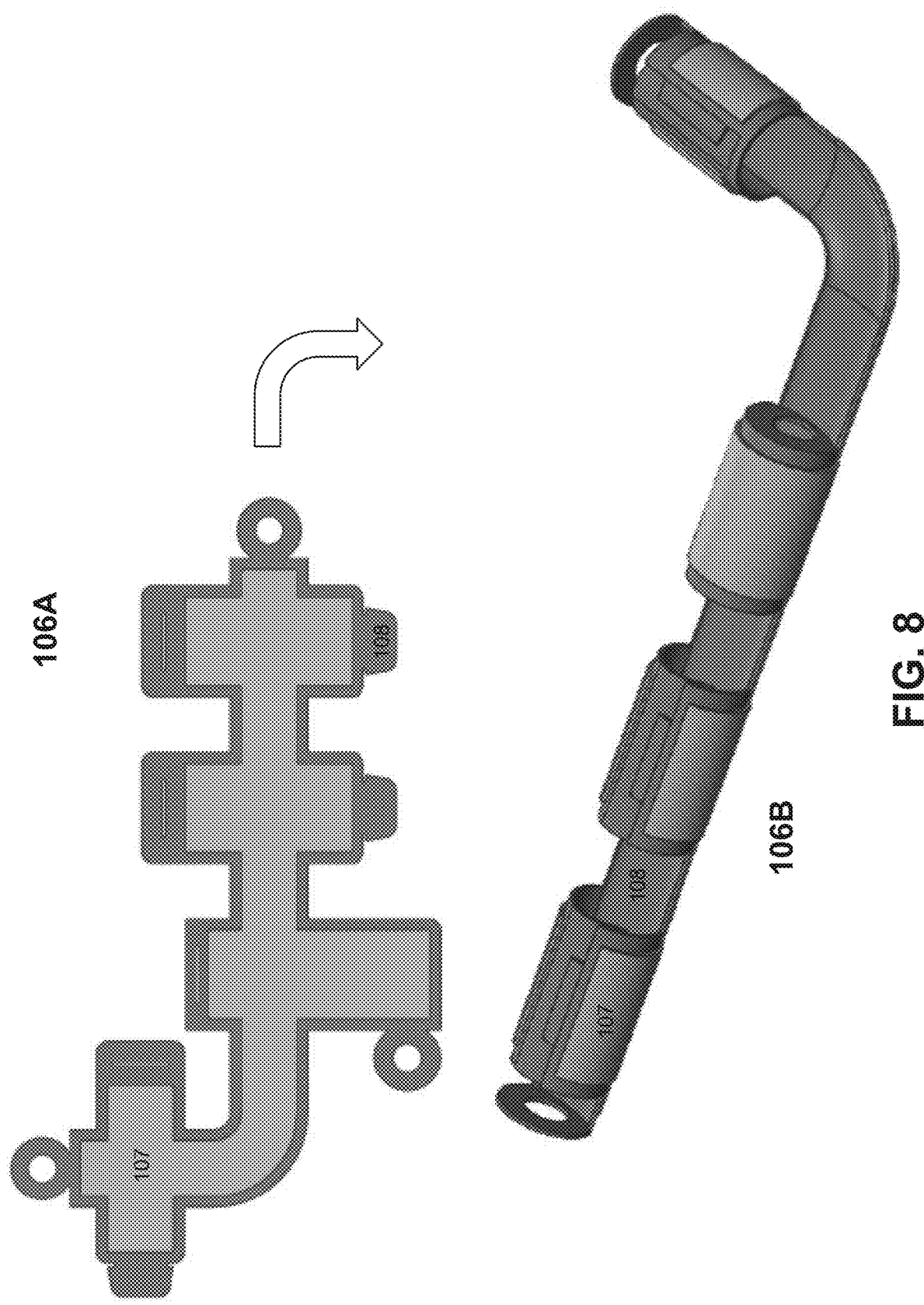
FIG. 8 illustrates an example configuration of a flex circuit of the microstimulator of FIG. 7.

As an alternative to FIG. 8, the flex circuit can be created by sputtering or depositing a biocompatible material onto the base layer that is pre-configured in the tubular cross-section. One example alternative is shown in FIG. 9, in which the metal is deposited directly onto the microstimulator in a defined way with very precise placement of the electrodes and plate metals. In this example, the base material 401 can be polyimide, silicone or polyurethane, other polymers, or other co-polymers. One or more metal layers (e.g., metal layer 402 that adheres better to the base layer 401, like titanium, and metal layer 403 like palladium) are then sputtered or deposited onto the tubular base 401 layer (e.g., the horizontal component of the microstimulator 201) directly. The amount of metal deposited may vary to allow for exposure to the tissue of the electrodes without exposing the plate. The base layer 401 can be configured, prior to deposition, into the J shape (90-degree shape between the vertical component and the horizontal component) required for the microstimulator. A second layer 402 (and subsequent layers 403) of material may be sputtered or deposited onto the base layer 401. An isolating material 404 can be applied of the same material as the base layer 401.

To create the right capacitive power transfer and to translate the waveform correctly, the dielectric constant must be created for the applications, which means adjusting the thickness of the metal, the surface area, etc. In an example, the tubular base layer is silicone. The dielectric created with the metal deposited onto the silicone will need to match the dielectric created in when the polyimide flex circuit is rolled to create the capacitor system for power transfer. Polyimide provides a significant contribution to the dielectric and thus if that is replaced with Silicone or other material as mentioned above, then the metal and position needs to be altered to match the dielectric constant. However, this process provides the advantage of reducing the amount of manual processing steps needed to manufacture the microstimulator. The other advantage of this technique is that delamination between the metal layer and the base layer is significantly reduced by depositing the metal onto the pre-formed tube base layer. When the flex circuit is rolled, certain areas see higher bend radii and hence are more susceptible to delamination events and thus causing further fallout in the manufacturing process.

Also important for the microstimulator is the overall stiffness of the flex circuit. A microstimulator at this scale, less than one mm in diameter and 5-6 mm in length, containing a full polyimide tube could cause the microstimulator to be quite rigid overall. To avoid this, the polyimide can be laser etched post deposition to create "bend joints" corresponding to areas in the microstimulator that are anticipated to have more flex and allow these areas to flex better. Using Silicone or Polyurethane as the base material will allow for ultimate flexibility, without having to laser etch areas out of the tubular cross-section to allow for bending of the microstimulator.

In another example, the electrodes can be mesh electrodes. Using mesh electrodes may eliminate the need for the radial channel extending from the central lumen 116 to wet the tissue surrounding the microstimulator. The mesh electrode allows for tear drainage from the central lumen through the mesh electrode. The mesh electrodes can be placed circumferentially around the entire microstimulator or can be placed and configured as directional electrodes. In other words, the electrodes are placed in a manner that is not circumferential, but sized and shaped accordingly to cover only a portion of the circumferential area of the microstimulator and allowing stimulation to occur in a directional manner. Alternatively, the directional electrodes can be made of a solid inert metal that is suitable for electrical stimulation or of a conductive polymer resin or other suitable material.

IV. Methods

Figure 13:
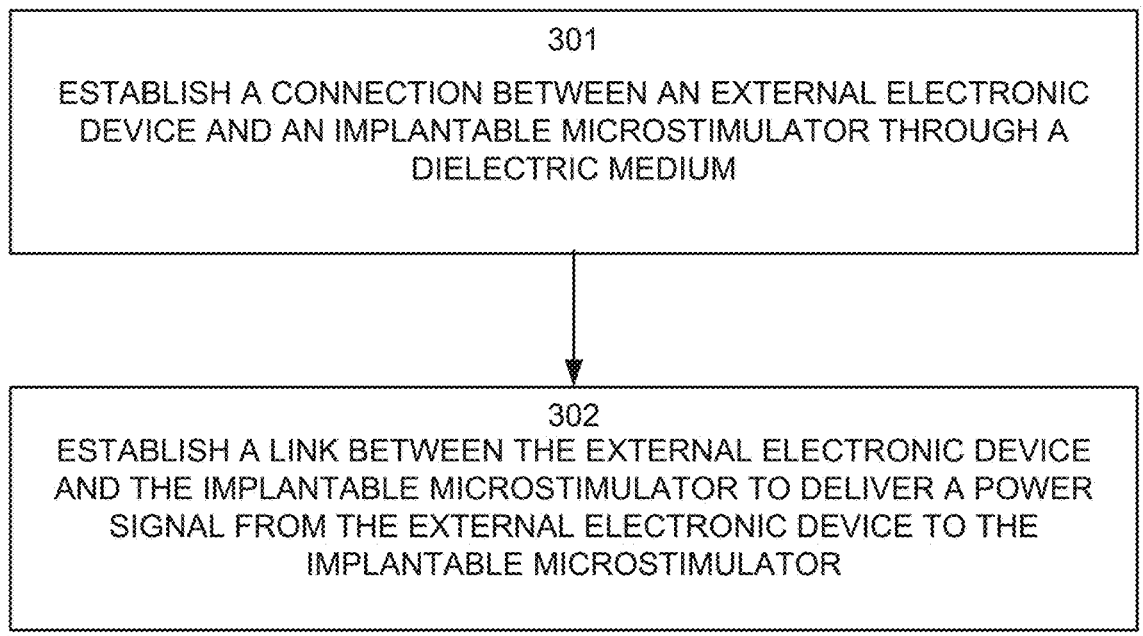
FIG. 13 illustrates a process flow diagram illustrating a method for powering an implantable microstimulator in accordance with another aspect of the present disclosure.
Figure 14:
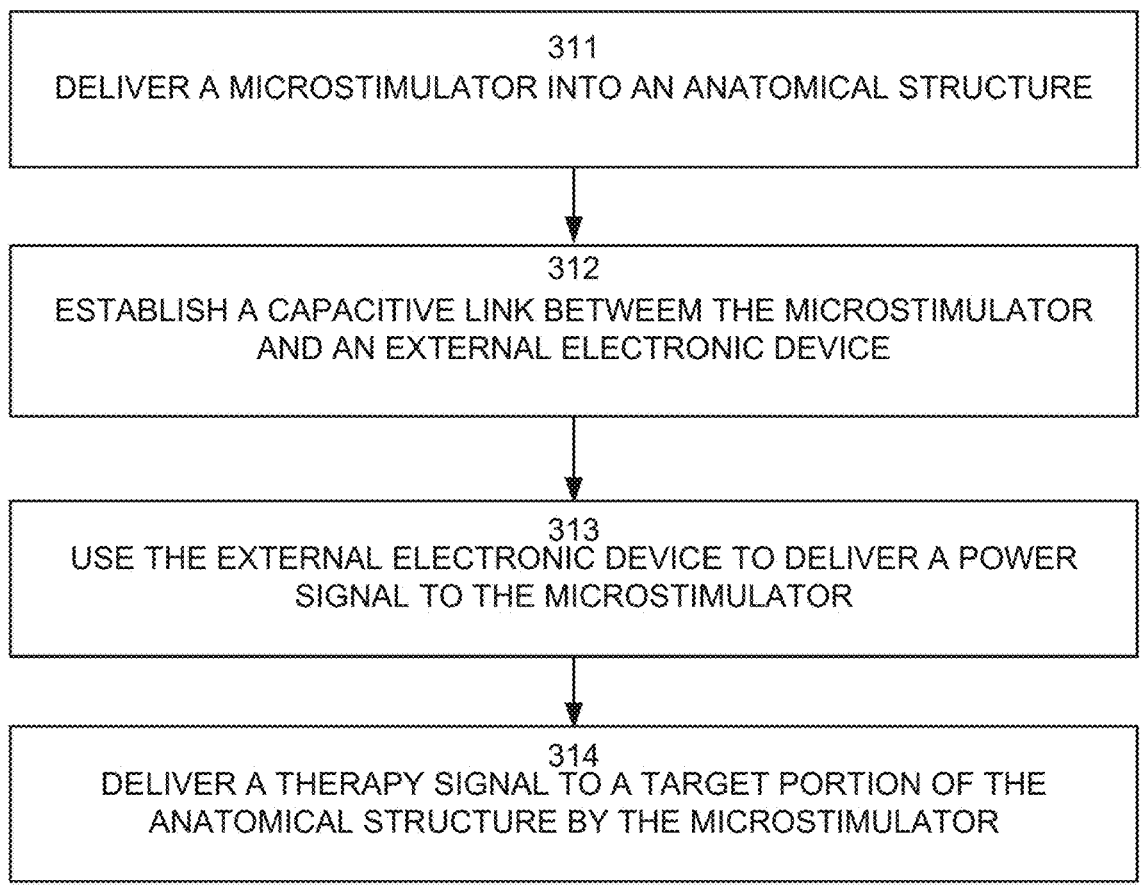
FIG. 14 illustrates a process flow diagram illustrating a method for treating, diagnosing, or preventing a medical condition in a subject in accordance with another aspect of the present disclosure.

Another aspect of the present disclosure can include methods for preventing, diagnosing, and/or treating one or more medical conditions. FIG. 13 illustrates a method for powering an implantable microstimulator. FIG. 14 illustrates a method for treating, diagnosing, or preventing a medical condition in a subject. The methods of FIGS. 13 and 14 can be implemented using the system of FIGS. 1-3, in which the implantable microstimulator may be as shown in FIGS. 7-12.

FIGS. 13 and 14, respectively, are illustrated as process flow diagrams with flowchart illustrations. For purposes of simplicity, the methods of FIGS. 13 and 14 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods of FIGS. 13 and 14. Additionally, FIGS. 13 and 14 may also include steps that can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

Referring to FIG. 13, an aspect of the present disclosure can include a method for powering an implantable microstimulator. As an example, the implantable microstimulator can be as shown in FIGS. 7-12, including a body and an electrically conductive insert. The powering can be through a wireless connection between the implantable microstimulator and an external electronic device. At 301, the connection can be established between the external electronic device and the implantable microstimulator through a dielectric material. The conductive material, in some examples, can be a biological material, such as the subject's skin. An example of this connection is shown in FIG. 2.

At 302, a link can be established between the external electronic device and the implantable microstimulator to deliver a power signal from the external electronic device to the implantable microstimulator. The link can be a capacitively coupled link link for capacitive power transfer upon a voltage change of an external plate associated with the external electronic device relative to an internal plate associated with the implantable microstimulator (shown in FIG. 2). The internal plate can be part of the electrically conductive insert within the body of the microstimulator. The electrically conductive insert can deliver a therapy signal (or stimulation signal) to the surrounding anatomical site in response to receiving the power signal.

Referring now to FIG. 14, illustrated is a method for treating, diagnosing, or preventing a medical condition in a subject. The medical condition can be an ocular, orbital, autoimmune, and/or neurological disease, disorder, and/or condition. Diseases that can be prevented, diagnosed, and/or treated can include, but are not limited to, dry eye, Meibomian gland dysfunction, goblet cell degranulation, presbyopia, Sjogren's syndrome, pain, ocular pain, corneal pain, facial pain, atypical facial pain, neuralgia, facial neuralgia, trigeminal neuralgia, ocular neuralgia, autonomic dysfunctions, headache, primary headache, secondary headache, myasthenia gravis, intravitreal injection side effects, and/or glaucoma. As another example, disorders that can be prevented, diagnosed, and/or treated can include, but are not limited to, contact lens over wear, contact lens keratopathy, contact lens intolerance, and/or ocular hypertension. Conditions that can be prevented, diagnosed, and/or treated can include, but are not limited to, loose skin, skin redness, lip ptosis, and/or winkles.

At 311, a microstimulator can be delivered into an anatomical structure of a subject. The anatomical structure can be any structure in the subject's body containing one or more target nerves. The microstimulator can be sized and dimensioned for the particular anatomical structure. For example, when inserted into a nasolacrimal structure, such as the punctum and canaliculus, to induce tear production, the microstimulator can be arranged in the shape shown in FIG. 7 with the dimensions described in connection to FIG. 7.

At 312, a capacitive link can be established between the microstimulator and an external electronic device. At 313, the external electronic device can be used to deliver a power signal to the microstimulator across the capacitive link. For example, the voltage of a plate of the external device can change relative to a plate of the internal device. As noted, "plates" is a general term describing a capacitive element; the "plates" are not necessarily shaped like plates. At 314, a therapy signal can be delivered by the microstimulator to a target portion of the anatomical structure. The target portion can include the one or more target nerves From the above description, those skilled in the art will perceive improvements, changes and modifications. Such improvements, changes and modifications are within the skill of one in the art and are intended to be covered by the appended claims.

What is claimed is:

1. A method for treating, diagnosing, or preventing a medical condition in a subject comprising:
    establishing a capacitive link between a microstimulator, positioned in an anatomical structure of the subject innervated by one or more nerves, the microstimulator comprising an internal conductive plate, and an external electronic device, comprising an external conductive plate, wherein the capacitive link comprises at least the external conductive plate and the internal conductive plate being aligned across a dielectric medium:
        wherein the microstimulator further comprises a body and an electrically conductive insert arranged within the body comprising the internal conductive plate and a power electrode, electrically connected to the internal conductive plate, and in physical contact a first portion of the anatomical structure, and a return electrode in physical contact with a second portion of the anatomical structure;
        wherein the power electrode and the return electrode are electrically isolated from each other within the microstimulator; and
    using the external electronic device to deliver a power signal to the internal conductive plate in the micrsotimulator through the capacitive link;
    wherein delivering the power signal to the microstimulator creates an electrical potential difference between the power electrode and the return electrode, and thereby generates a therapy signal comprising an electrical field that is delivered directly to a target portion of the anatomical structure.

2. The method of claim 1, wherein the body comprises a horizontal portion, a vertical portion, and a curved portion extending between and connecting the horizontal portion and the vertical portion,
    wherein the horizontal portion and the vertical portion are arranged at an angle relative to one another, and wherein the horizontal portion is longer than the vertical portion.

3. The method of claim 1, wherein the therapy signal is configured to treat and/or diagnose a neurological disease.

4. The method of claim 3, wherein the neurological disease is at least one of dry eye, Meibomian gland dysfunction, goblet cell degranulation, presbyopia, Sjogren's syndrome, pain, ocular pain, corneal pain, facial pain, atypical facial pain, neuralgia, facial neuralgia, trigeminal neuralgia, ocular neuralgia, autonomic dysfunctions, headache, primary headache, secondary headache, myasthenia gravis, intravitreal injection side effects, contact lens intolerance, contact lens over wear, contact lens keratopathy or glaucoma.

5. The method of claim 1, wherein the therapy signal is configured to treat and/or diagnose an ocular disorder.

6. The method of claim 5, wherein the ocular disorder is ocular hypertension.

7. The method of claim 1, wherein the therapy signal is configured to induce a neurological reflex to provide a therapeutic effect.

8. The method of claim 7, wherein the therapeutic effect is at least one of upregulation or downregulation of one or more cellular pathways to treat a neurological disease.

9. The method of claim 1, wherein the therapy signal is configured to tighten skin, reduce skin redness, treat lid ptosis, or reduce wrinkles.

10. The method of claim 1, wherein the therapy signal is delivered at least one of prior to a surgical procedure, during the surgical procedure, and after a surgical procedure.

11. The method of claim 1, wherein the electrical field is generated from current flow through a portion of the subject between the power electrode and the return electrode.

12. The method of claim 11, wherein the current is generated in response to changing impedance of the capacitive link.

13. The method of claim 1, wherein the anatomical structure of the subject innervated by one or more nerves comprises a nasolacrimal drainage system of the subject.

14. The method of claim 1, wherein the internal conductive plate is curved.

15. The method of claim 1, wherein the external conductive plate and the internal conductive plate are aligned in a generally parallel configuration across the dielectric medium.

16. The method of claim 1, wherein establishing the capacitive link comprises varying a voltage at the external conductive plate.

* * * * *